(12) United States Patent
Jerde et al.

(10) Patent No.: US 7,780,637 B2
(45) Date of Patent: Aug. 24, 2010

(54) MEDICAL DEVICE CONTAINER

(75) Inventors: Steven Jerde, 1920 Wilshire Dr. Northeast, Rochester, MN (US) 55906; Steven Huebl, Jordan, MN (US)

(73) Assignee: Steven Jerde, Rochester, MN (US)

( * ) Notice: Subject to any disclaimer, the term of this patent is extended or adjusted under 35 U.S.C. 154(b) by 0 days.

(21) Appl. No.: 11/836,218

(22) Filed: Aug. 9, 2007

(65) Prior Publication Data
US 2008/0108951 A1 May 8, 2008

Related U.S. Application Data

(60) Provisional application No. 60/856,828, filed on Nov. 6, 2006.

(51) Int. Cl.
*A61M 5/32* (2006.01)

(52) U.S. Cl. ...................... 604/192; 604/110

(58) Field of Classification Search .......... 604/68, 604/110, 192, 193, 198, 232, 263; 128/DIG. 1; 206/363–370; 606/181, 182, 583
See application file for complete search history.

(56) References Cited

U.S. PATENT DOCUMENTS

| | | | |
|---|---|---|---|
| 5,931,817 A * | 8/1999 | Nguyen et al. | 604/263 |
| 6,379,339 B1 | 4/2002 | Klitgaard et al. | |
| 6,585,698 B1 * | 7/2003 | Packman et al. | 604/207 |
| 6,869,418 B2 * | 3/2005 | Marano-Ford | 604/192 |
| 2003/0078543 A1 * | 4/2003 | Bergeron et al. | 604/192 |
| 2005/0065481 A1 * | 3/2005 | Hauri et al. | 604/263 |

OTHER PUBLICATIONS

Eli Lilly and Co., Indianapolis, IN 46285, USA Literature/PV 3734 AMP Humalog Humulin-pen-user manual (web link- http://pi.lilly.com/us/humalog_humulin-pen-user_manual.pdf).

* cited by examiner

*Primary Examiner*—Kevin C Sirmons
*Assistant Examiner*—Emily Schmidt
(74) *Attorney, Agent, or Firm*—Patterson Thuente Christensen Pedersen, P.A.

(57) ABSTRACT

A storage system for a needleless pen delivery device syringe and a hypodermic needle adapted for attachment to and use with the pen delivery device syringe. A tubular sleeve has a first hollow chamber for receiving therein the needleless pen delivery device syringe, and a hollow cap has a second hollow chamber for receiving therein the hypodermic needle. The cap is adapted to affix to the sleeve to form a continuous tubular housing, and the sleeve is adapted to receive the pen delivery device syringe only when the needle is not attached to the syringe. Alternative exemplary embodiments provide for storing other related accessories or additional spare needles.

13 Claims, 12 Drawing Sheets

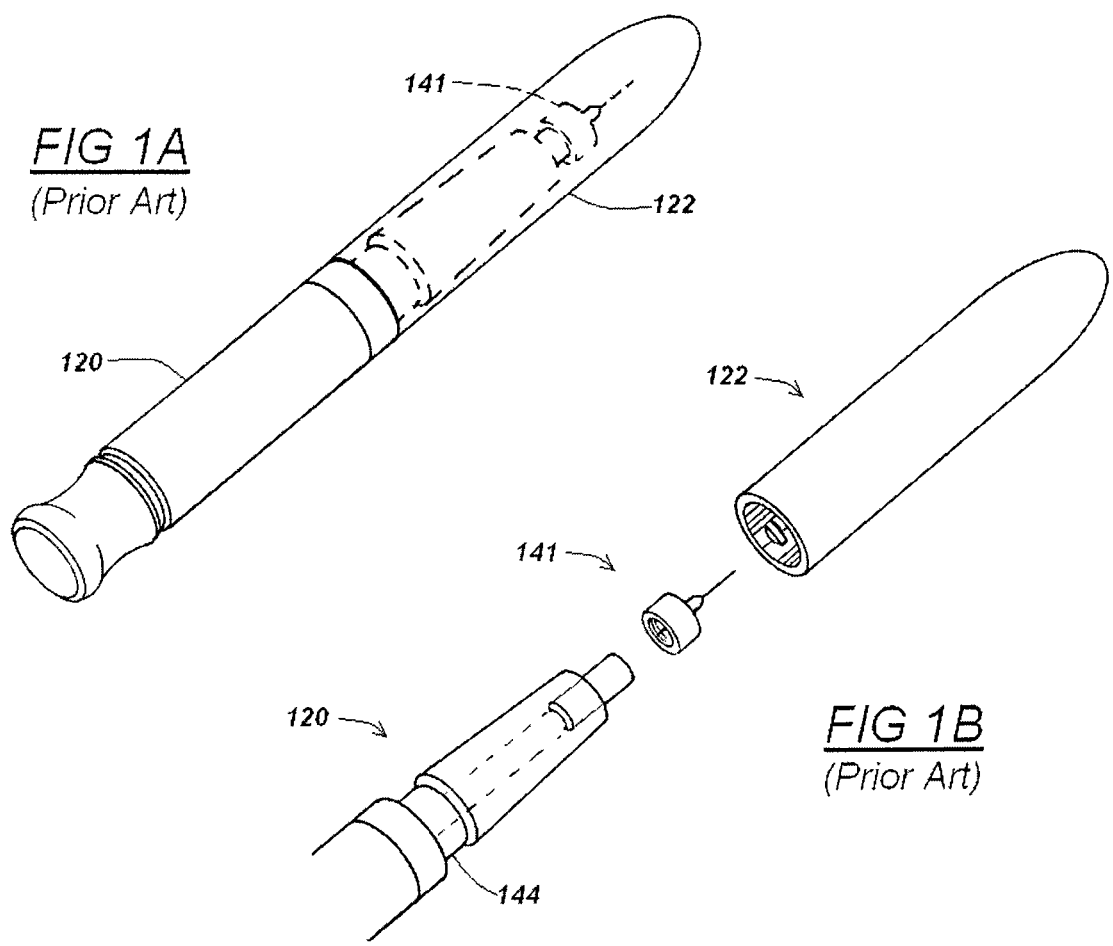

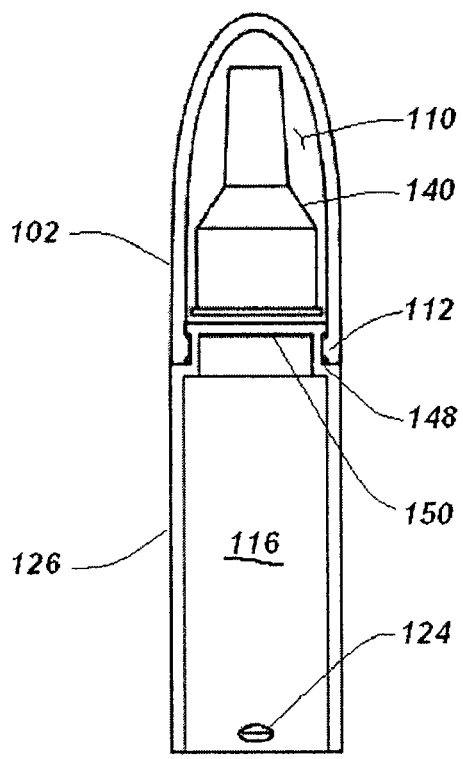
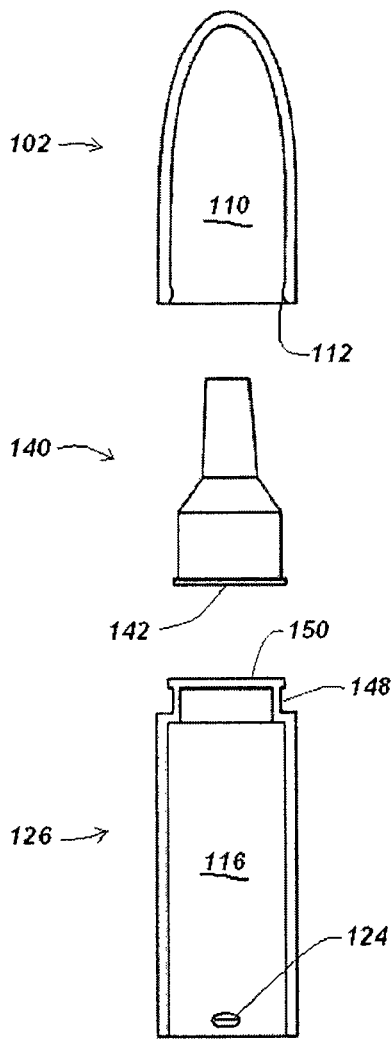
FIG 2C
FIG 2D

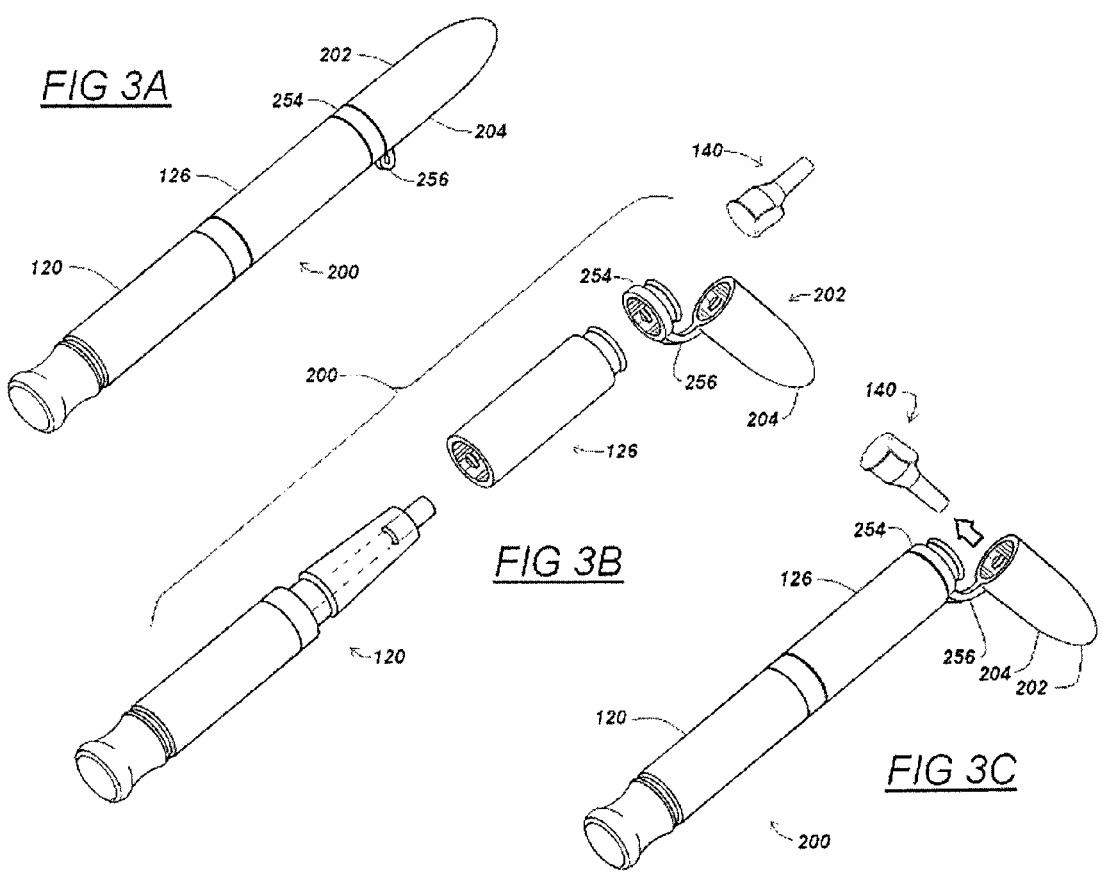

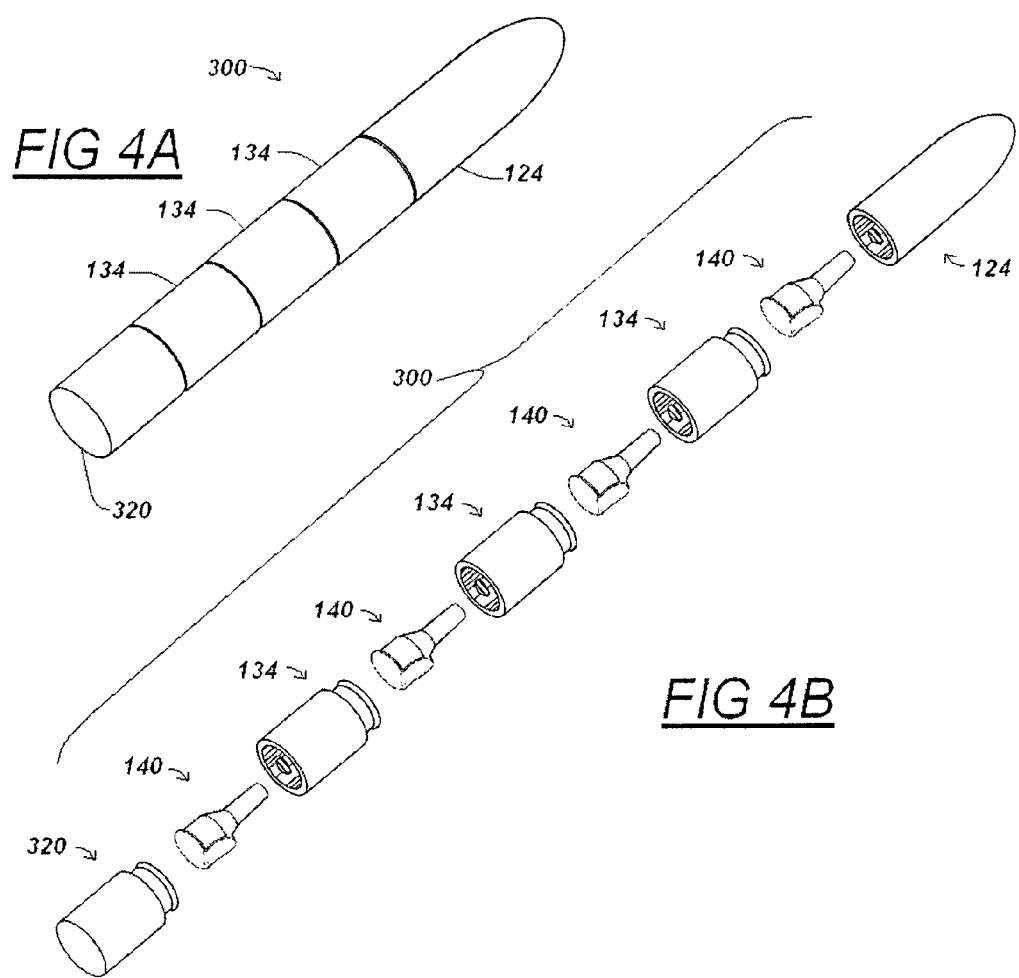

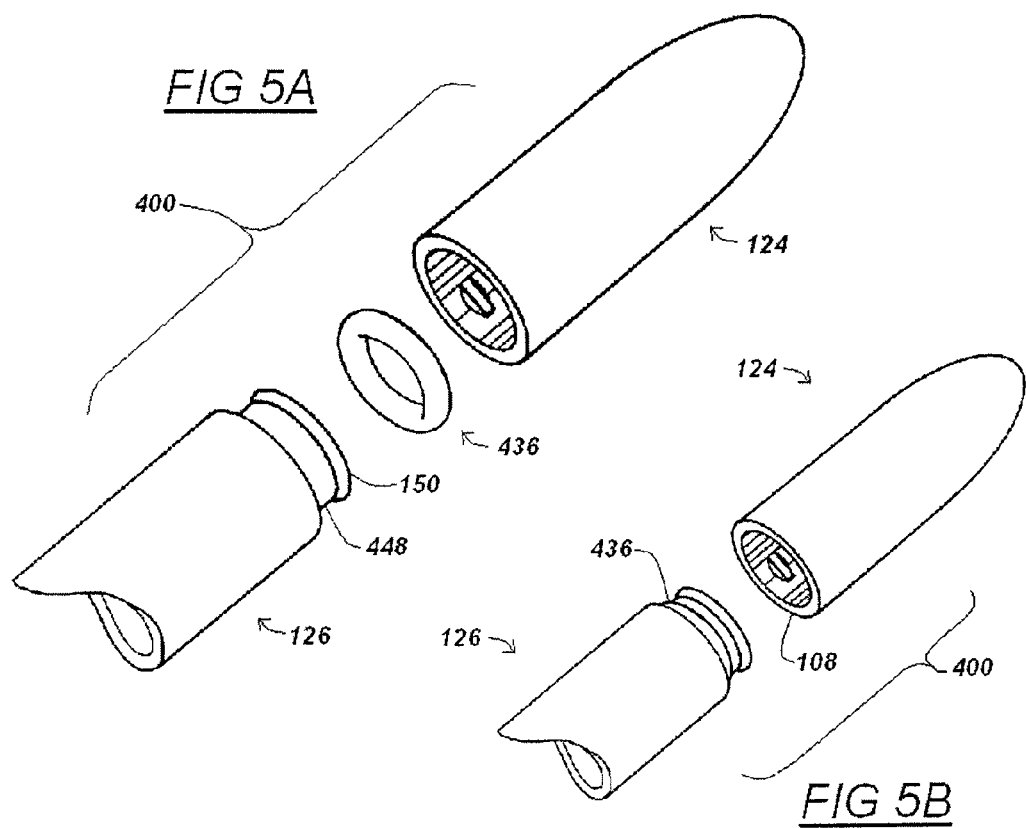

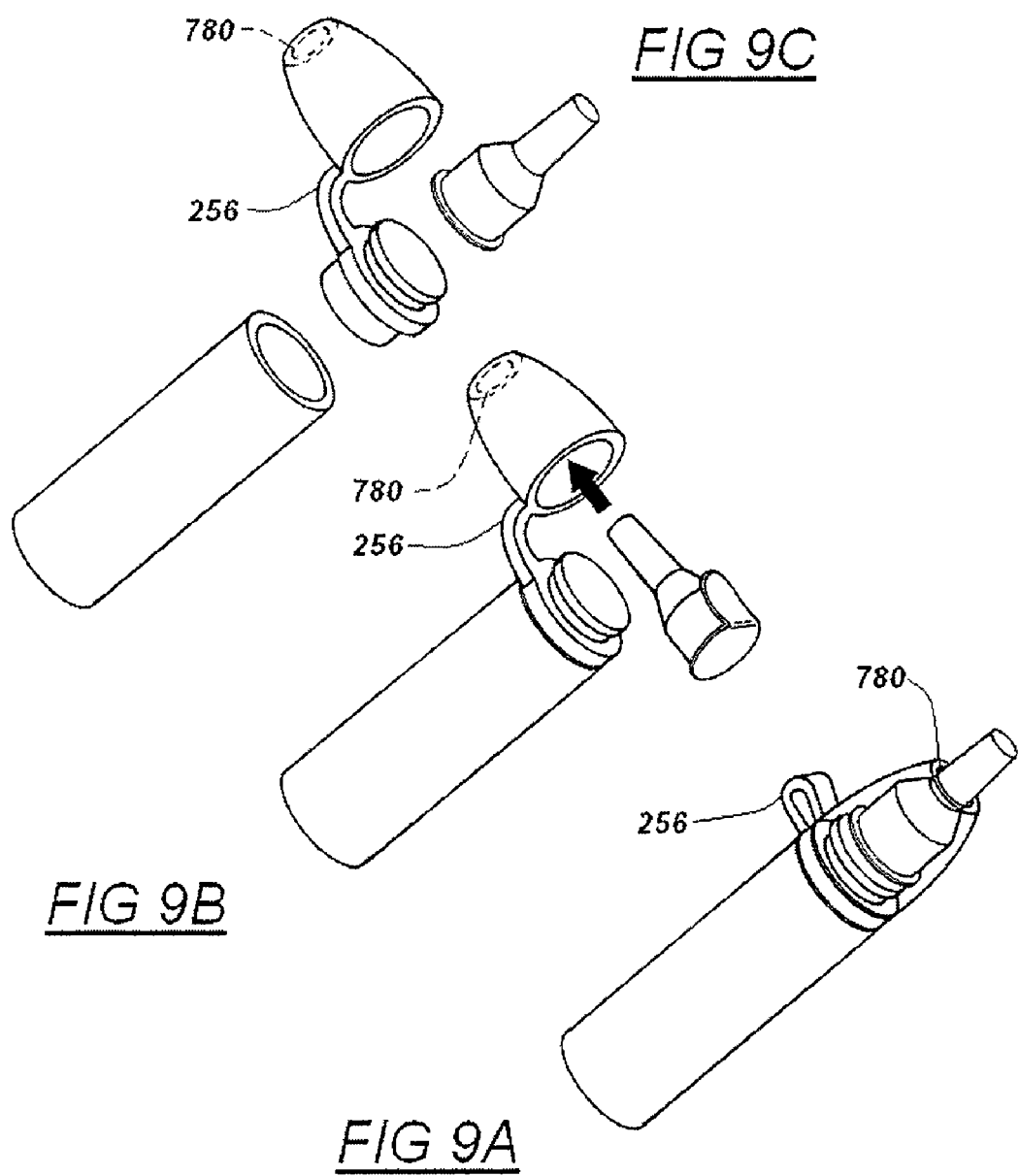

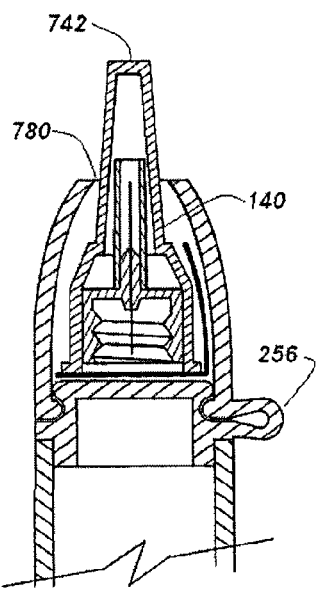
FIG 9D
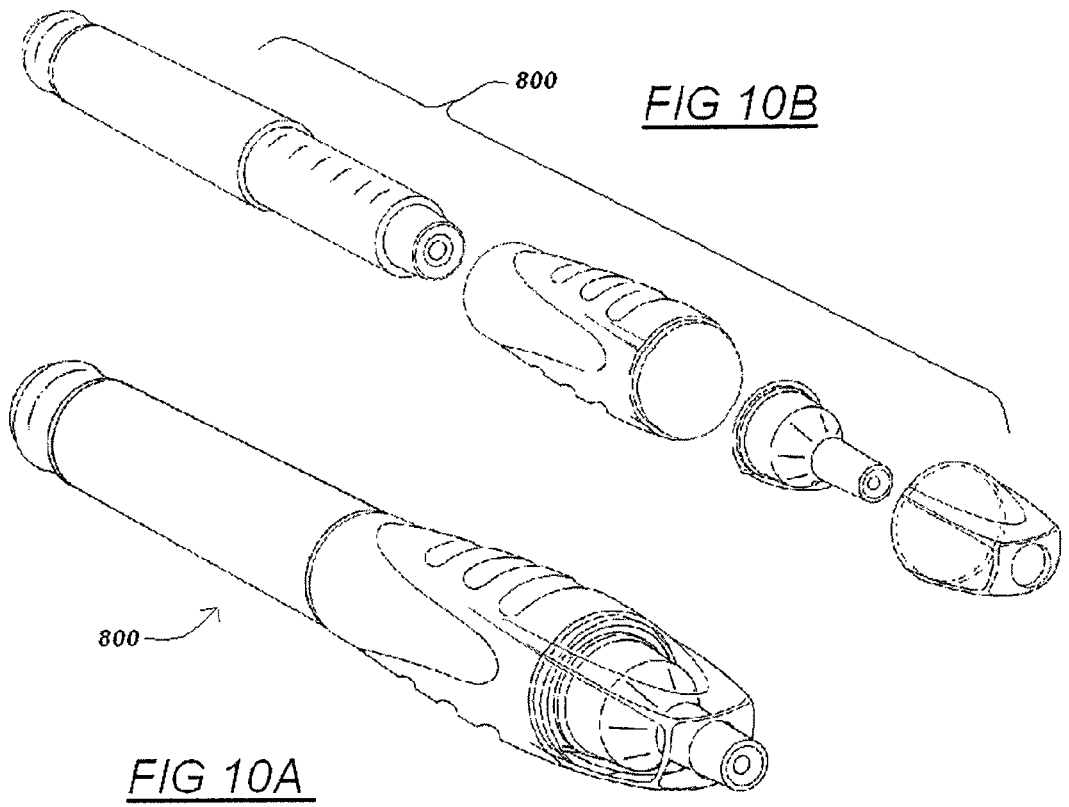
FIG 10B
FIG 10A

MEDICAL DEVICE CONTAINER

RELATED APPLICATION

This application claims the benefit of U.S. Provisional Application No. 60/856,828, filed Nov. 6, 2006. The entire teachings of the referenced application are incorporated herein by reference.

BACKGROUND OF THE INVENTION

Medical delivery devices employing a pen delivery device syringe with a replaceable hypodermic pen needle are well known and used to meter the proper dosage of insulin and other medications, such as to self-users who administer their own injections. While pen delivery device syringes are typically provided with enough insulin for several doses, the removable and replaceable needles are intended for single use only. For safety and sanitation, it is recommended by the pen delivery device manufacturer's FDA approved Package Insert, that the needles of such existing devices should not remain attached to the pen delivery device syringe after use, and should be used only once, then discarded. This creates the need for a new sterile needle whenever and wherever the next injection is necessary, and the need to carry additional needles with the delivery device.

To use a needle for the first time, it must be unsealed, screwed to the pen delivery device syringe, the outer cap must be removed, and then the inner cap must be removed, leaving possible the inhalation of air into the pen delivery device syringe if the needle is not removed between injections. The outer cap is used to remove the pen needle, and is manufactured so as to not allow the needle to penetrate the cap. The inner cap is not meant for reuse of any kind. If the inner cap is used to recap the needle the needle can penetrate the inner cap and cause a stab wound. But since many users are inclined, for reasons of economy of out of laziness, to leave a pen needle attached to the pen delivery device syringe and re-use the pen needle, a serious safety hazard results even in a storage system that contains the pen needle outer cap to protect from inadvertent pricking. This safety concern and the inclination to disobey recommended needle replacement instructions also creates the need for a system that forces users to separate the needle from the syringe after each use.

Containers are well known for carrying both delivery devices and extra needles, such those sold by Eli Lilly and Company of Indianapolis, Ind., which is depicted schematically in FIGS. 1A and 1B of this disclosure. As seen in FIGS. 1A and 1B, this syringe 120 includes a dust cover 122 which is large enough to hold a new needle 141 without a protective case. As will be shown in later drawings, such as FIG. 2B, such needles are normally provided in a protective needle case, and intended to be stored and protected in the dust cover 122 in a sealed state, removed, unsealed, and affixed to the pen delivery device syringe just prior to use, and then removed and discarded after use. But rather than provide a means to force users to remove and discard used needles, these systems actually inspire users to leave the used pen needles attached to the pen delivery device syringe by providing a dust cover with sufficient space to fit back onto the syringe with the used needle still attached.

For use, a patient carrying the pen delivery device syringe 120 of FIGS. 1A and 1B and finding himself in need of an injection would first remove dust cover 122, which may be affixed by a snap-fit or by threading, find a pen needle in a pocket, purse or medicine cabinet, remove the pen needle's protective foil cover, attach the needle to the pen delivery device syringe, remove the outer cap of the pen needle, remove the inner cap of the pen needle and then give themselves an injection with the attached pen needle. A dose of insulin is then administered by injection to the patient. The used needle should finally be, replaced into its protective outer cap casing 140, and discarded.

It should be appreciated however upon inspection of FIG. 1A that there is plenty of room within dust cover 122 to receive again the pen delivery device syringe with the used needle left still attached without its outer cover, and it should be appreciated how such a possibility increases the likelihood that such an improper practice my be followed by many forgetful, frugal, or lazy patients.

Additionally, many users may require more than a single dose of insulin during the day or may require a low does that allows them to use the pen delivery device syringe several times, and it is preferred that several spare needles be on hand for each syringe. But existing syringes, such as that shown in FIGS. 1A and 1B have space to hold only a single new needle, without the outer cap, thereby forcing users to carry spare needles separately or inspiring them to improperly leave used needles attached to the syringe for dangerous re-use and the possibility of inhalation of oxygen into the syringe.

It is well known that many pieces of apparel, purses, pocket books, portfolios, brief cases, and similar items worn or carried during everyday travels have receiving means specifically shaped to accommodate pens and pencils. For various reasons including optimized carrying in such receiving means, the aforementioned prior art pen delivery device syringes are housed in containers shaped like typical writing pens, generally having a tubular housing with a blunt bullet-shaped tip. The bullet shaped tip is safer than a sharply pointed tip, while still pointed enough to aid in the insertion of the housing into a pocket or such. And since most diabetics prefer to remain discreet about their illnesses, the ability of the pen-shaped device to be carried and stowed discreetly is of significant value. A pen-shaped housed syringe is as discreet and easy to carry as ordinary pens and readily received within typical pen receiving means.

The lack of a storage location for more than a single replacement needle on or within the housings of such pen delivery device syringes has forced their users to carry accessory packs or other containers to hold their spare needles, which are not discreet or as readily stored and carried as the pen-shaped device itself, and which further inspire users to improperly re-use pen needles. Users who do obey the recommendations of syringe manufacturers and remove needles after each use are forced to carry their spare needles separately and less accessibly, and often complain about misplacing or forgetting needles and about the inconvenience of managing two or three different objects (syringes, needles, and containers). The benefits of the discreet and convenient pen-shaped devices are often lost due to such multiple object management.

Additionally, in the panic of an emergency, users have been known to fumble while looking through a purse or pockets for a lost spare needle which was unable to be stored with the delivery device or in the pen receiving means of the purse or apparel, thereby losing critical time for administering their medication.

There exists therefore the need for a compact and pen-shaped storage system for complimentary use with or for containing a pen-shaped syringe and one or more spare needles, which is capable of being received and carried as an ordinary pen, and which keeps both the delivery device and pen needle for instant access as needed, yet which forces the pen delivery device syringe and needle to be separated both before and after use.

Additionally, because people with diabetes are the primary users of such medical delivery devices and typically need to monitor their blood sugar levels with the use of disposable self-monitoring blood glucose strips, and because these strips should be kept in an airtight container, there exists the further need for such a compact and pen-shaped storage system which may also contain such strips or other related accessories.

SUMMARY OF THE INVENTION

The present invention may be embodied as a pen-shaped storage system for complimentary use with a variety of devices including pen delivery device syringes, including a pen needle storage compartment or a plurality of pen needle/accessory storage compartments, and which system is capable of being received and carried as an ordinary pen, and which may keep in separation the pen delivery device syringe, the one or more pen needles, and the other related accessories, for instant access as needed, and which forces the user to remove a used pen needle from the pen delivery device syringe prior to re-storage.

Having an integrated system, which includes the container, the pen delivery device syringe, the pen needle, and related accessories within the same convenient, compact, discreet, and readily accessible unitary tubular structure, is found to solve the aforementioned organizational and storage deficiencies of the prior art. Forcing the separation of the used pen needle from the syringe before allowing re-storage is found to solve the safety concerns associated with the improper re-use of pen needles The present invention may be embodied as an easy-to-carry pen-shaped containment system for including, holding, or attaching to a syringe, and having one or more storage compartments which may be used for storing and carrying pen needles or other accessories separately from the pen delivery device syringe.

The disclosed storage systems are simple in construction and inexpensive to manufacture. The systems may be completely assembled and used with any number of medical or other devices to hold and organize accessories. The disclosed systems are most specifically intended for use in medical insulin delivery, utilizing the storage container as a space to hold required components for the delivery of insulin, but may be adaptable to use in any similar pen delivery device activity. The systems disclosed, according to just an exemplary few of the near infinite number of possible embodiments of the invention, may provide improved accessibility to the pen delivery device syringe and sterile injection pen needles, and improved safety, over prior art storage systems and techniques.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention.

FIG. 1A is a perspective view of a pen delivery device syringe of the prior art including stored within its dust cover an attached needle without the needle having the outer cover in place.

FIG. 1B is a partial exploded view of the pen delivery device syringe, pen needle, and dust cover of FIG. 1A, FIG. 2C is a cross-sectional view through the storage cap and dust sleeve of FIG. 2A, showing the pen needle stored therein, FIG. 2D is an exploded cross-sectional view through the storage cap and dust sleeve of FIG. 2C, FIG. 3A is a perspective view of a second exemplary embodiment of the invention including the a storage cap hinged formed with a dust sleeve, which is in turn attached to a pen delivery device syringe, FIG. 3B is an exploded view of the storage cap, dust sleeve, and pen delivery device syringe of FIG. 3A, FIG. 3C is a perspective view of the embodiment of FIG. 3A with the storage cap hinged open to allow access to the pen needle stored within, FIG. 4A is a perspective view of a third exemplary embodiment of the invention including the a storage cap attached to a series of intermediary pen needle or accessory storage compartments, which are attached either to an end cap, FIG. 4B is an exploded view of the embodiment of FIG. 4A, FIG. 5A is a partial exploded view of a fourth embodiment of the invention including an o-ring for air-tight sealing at the storage cap connection, FIG. 5B is a partial exploded view of the embodiment of FIG. 5A showing the storage cap removed and the o-ring attached, FIG. 9A is a perspective view of an embodiment of the invention having a pen needle ejection hole in the cap and having the cap hinged formed with the dust sleeve, FIG. 9B is a perspective view of the embodiment of FIG. 9A showing the cap in its open position about the hinge, FIG. 9C is an exploded view of the embodiment of FIG. 9A, FIG. 9D is a partial cross-sectional view through the embodiment of FIG. 9A, FIG. 10A is a perspective view of an ornamentally styled embodiment of the invention, FIG. 10B is an exploded view of the embodiment of FIG. 10A.

DETAILED DESCRIPTION OF THE INVENTION

Figure 2A:
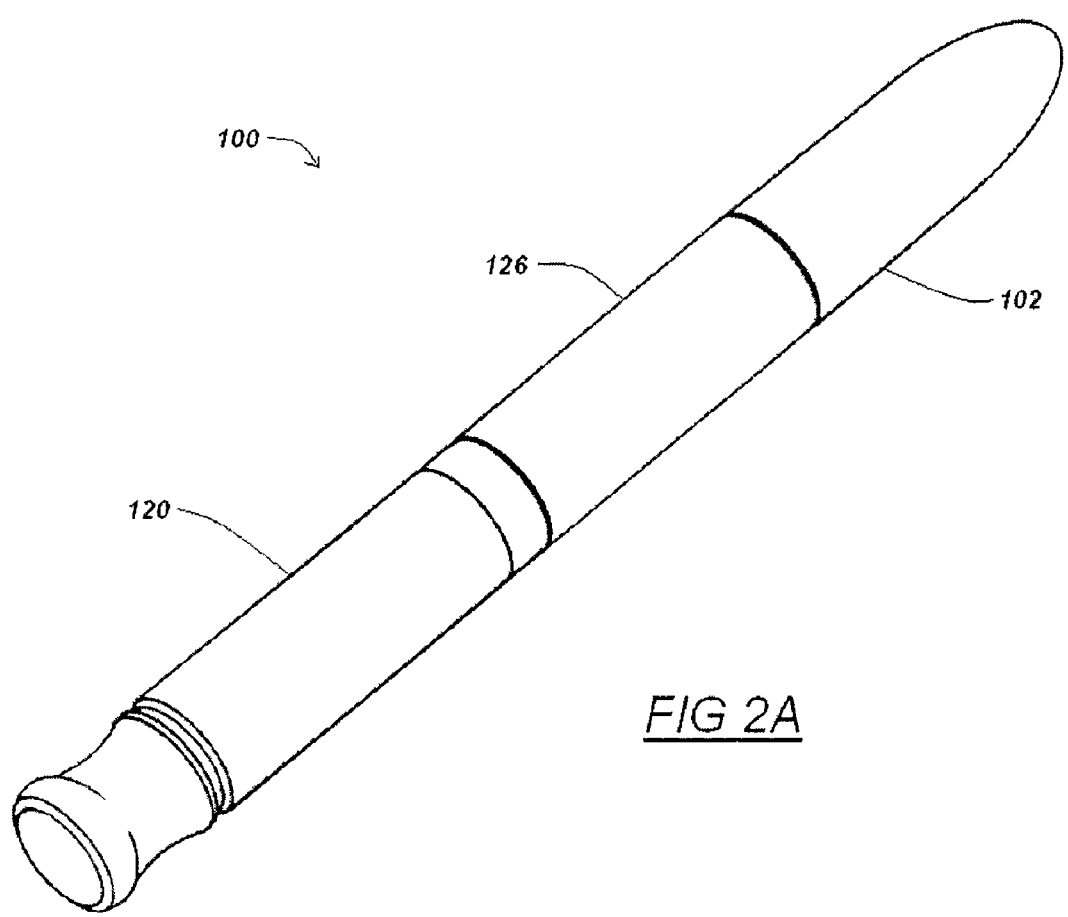
FIG. 2A is a perspective view of a first exemplary storage system according to the invention having a pen needle storage cap attached to a dust sleeve, which is in turn attached to a pen delivery device syringe.
Figure 2B:
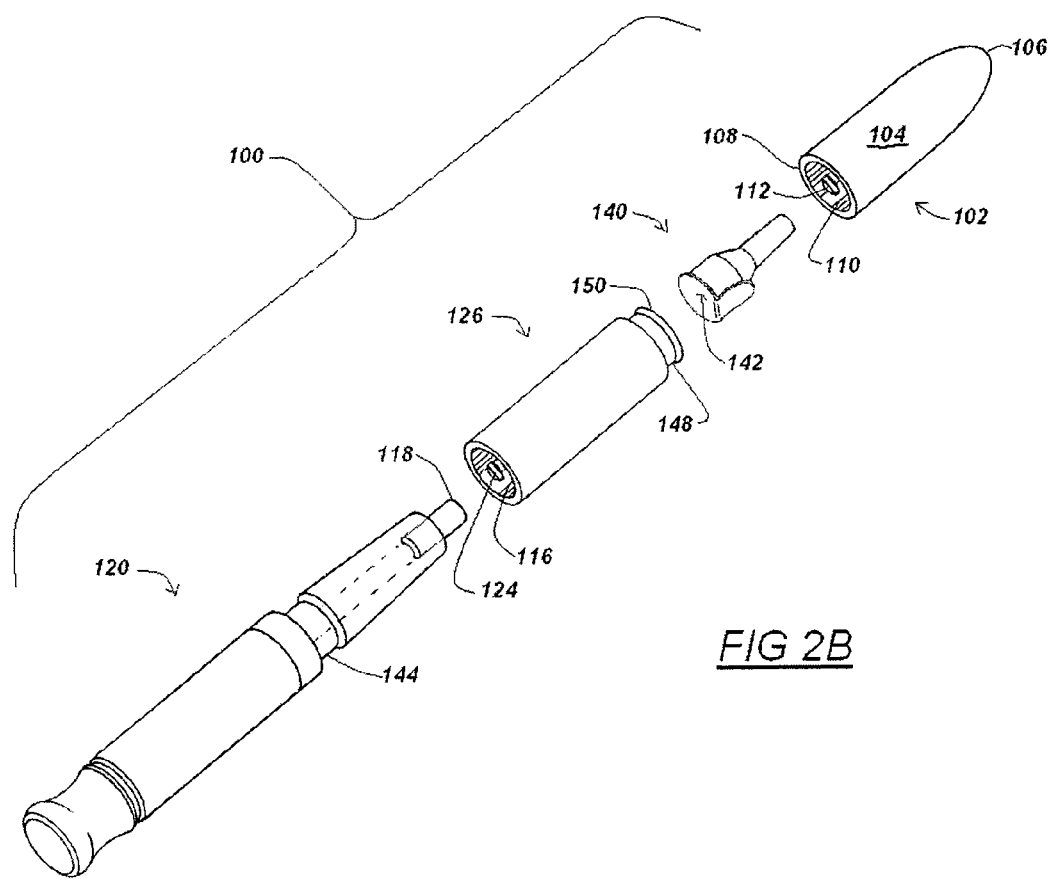
FIG. 2B is an exploded view of the storage cap, dust sleeve, pen needle, and syringe of FIG. 2A.

Reference will be made to the appended FIGS. 2A through 11, where there are shown numerous exemplary embodiments of storage systems for use with insulin delivering pen syringes, in accordance with the invention. In the drawings, like reference numerals designate corresponding parts throughout the views.

Referring to FIGS. 2A through 2D, system 100 has an open-ended cap 102 with an outer shell 104 having a blunt bullet-shaped first end 106 and a circular second end 108 opposite the first end. A cavity 110 is defined within the shell 104 and has detents 112 for snap-fitted and removable attachment of cap 102 to dust sleeve 126 at peripheral groove 148. Dust sleeve 126 includes hollow cavity 116, which includes similar detents 124 for snap-fitted and removable attachment to a typical insulin pen delivery device syringe 120 at peripheral groove 144.

Pen delivery device syringe 120 typically includes one or more doses of insulin. Cap 102 and sleeve 126 may alternatively be attached by another suitable attachment means, such as threading.

Cavity 110 is adapted to receive a typical pen needle assembly 140 including a needle such as needle 141 of FIGS. 1A and 1B. To access the needle assembly, cap 102 must first be removed from sleeve 126, then needle assembly 140 is removed from cavity 110. Needle assembly 140 typically includes a protective foil seal 142, and outer and inner caps which must be removed for access to the needle within. Dust sleeve 126 is removed from pen delivery device syringe 120 so that the pen needle may next be affixed to the pen delivery device syringe's distal end 118 and a dose of insulin may then be administered by hypodermic injection.

After injection, the needle is removed from the syringe and returned to within the protective case of assembly 140 and appropriated discarded. Failure to remove the pen needle from the pen delivery device syringe denies replacement of dust sleeve, 126, because the sleeve's distal end 150 would interfere with the pen needle and damage the hypodermic needle making reuse impossible were it not removed. This forces the user to remove the needle. With the needle properly removed using the outer pen needle cap, dust sleeve 126 and cap 102 may be reattached and the assemble may be returned to storage in its original compact and convenient state.

While not shown, it is noted that the detents 124 are conveniently adapted to receive the distal end 150 and peripheral groove 148 of another identical dust sleeve, which then receives pen delivery device syringe 120. Such an arrangement allows the system of FIGS. 2A to 2D to be adapted to accommodate any reasonable number of additional dust sleeves in series connection, which can thus be used to store extra needles and other accessories.

In a second exemplary embodiment, shown in FIGS. 3A through 3C, storage system 200 is shown, having a pen needle storage cap 202 that includes collar 254, which removably snap-fits to dust sleeve 126, and which in turn removably snap fits to the pen delivery device syringe 120. Collar 254 is integrally formed with shell 204 through flexible living hinge member 256, thereby preventing loss of shell 204 when it is hinged opened as shown in FIGS. 3B and 3C for similar access to the needle assembly (not shown). Otherwise, use and operation of this embodiment is the same as the first embodiment. Hinge member 256 is preferably co-molded with collar 254 and cap 202 of a flexible polymer material such as polypropylene or the like, to allow for repeated flexures of the hinge without breakage.

Referring now to FIGS. 4A and 4B, there is shown a storage system 300 in which needle-storing cap 124 may be used in conjunction with a selectable plurality of needle-storing or accessory-storing modules 134. Each module adapted similarly to the cap for receiving and storing either a needle assembly 140 in the same manner as the caps of the previous embodiments, or some other accessories such as blood monitoring strips (not shown), with the last module being snap-fitted to a terminal end plug 320. The connections of the modules together and to the terminal end cap may also be made by other means, such as threading. And rather than the terminal end cap shown, the last module may alternatively be a dust sleeve such as sleeve 126 in FIG. 2A, which may then receive a pen delivery device syringe. Such a system allows the user to carry numerous pen needles and accessories according to his expected needs, all in one convenient pen-shaped package that can be conveniently stored and transported as an ordinary pen.

FIGS. 5A and 5B depict a storage system 400 which is an alternate embodiment of the foregoing systems only in that a gasket, such as but not limited to o-ring 436 is used to provide an air-tight seal between cap 124 and dust sleeve 126. O-ring 436 is fitted over the sleeve's distal end 150 and into peripheral groove 448, to provide a seal against the cap's circular open end 108 when the cap is fitted to the sleeve.

Figure 6:
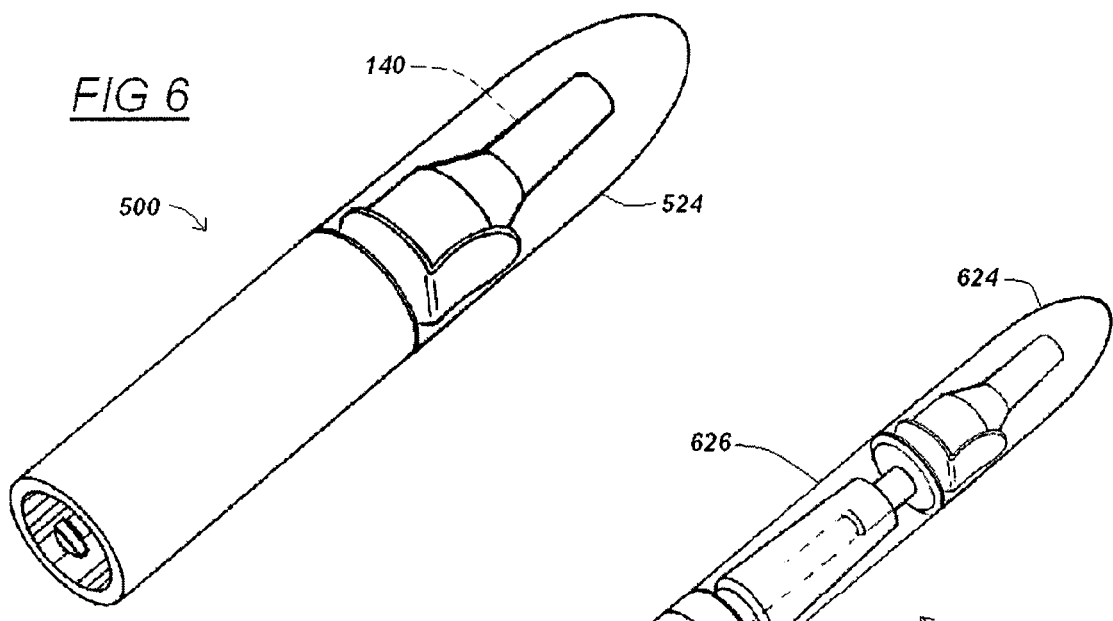
FIG. 6 is a perspective view of a fifth embodiment of the invention having a transparent needle storage cap.

FIG. 6 shows a storage system 500, which could be identical to any of the other embodiments except that cap 524 may be molded of a transparent or tinted material so that the needle assembly 140 can be viewed without disassembly.

Figure 7:
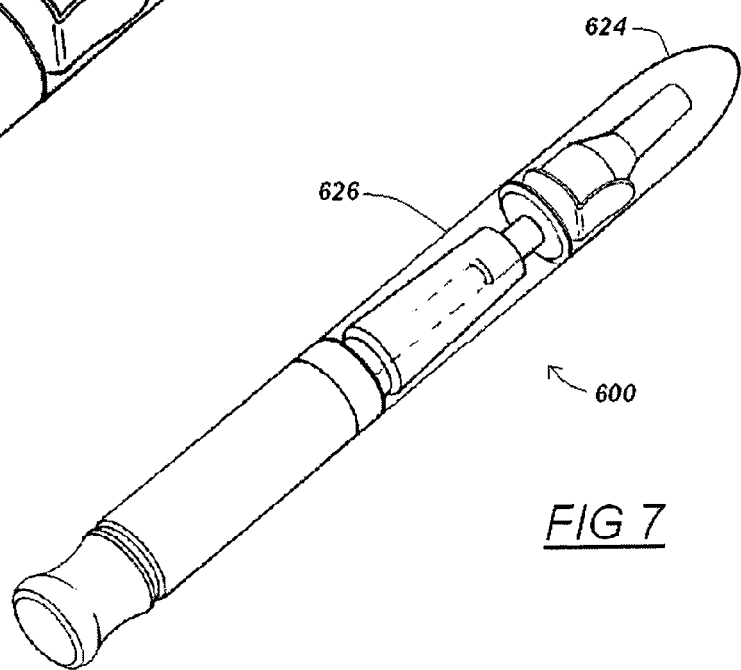
FIG. 7 is a perspective view of a sixth embodiment of the invention having a transparent storage cap and a transparent dust sleeve.

FIG. 7 shows a storage system 600, which could be identical to any of the other embodiments except that cap 624, and dust sleeve 626 may be molded of a clear or tinted material so that the contents can be viewed without disassembly.

Figure 8A:
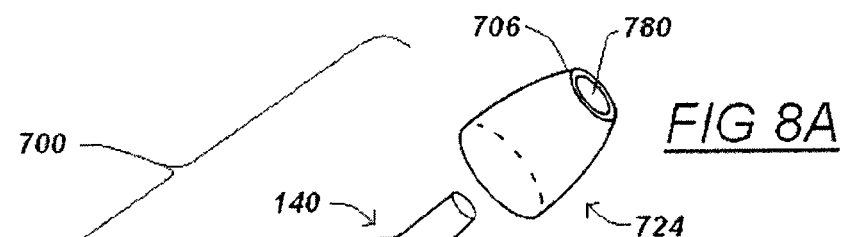
FIG. 8A is an exploded view of an seventh embodiment of the invention having a pen needle ejecting hole in the needle storage cap.
Figure 8B:
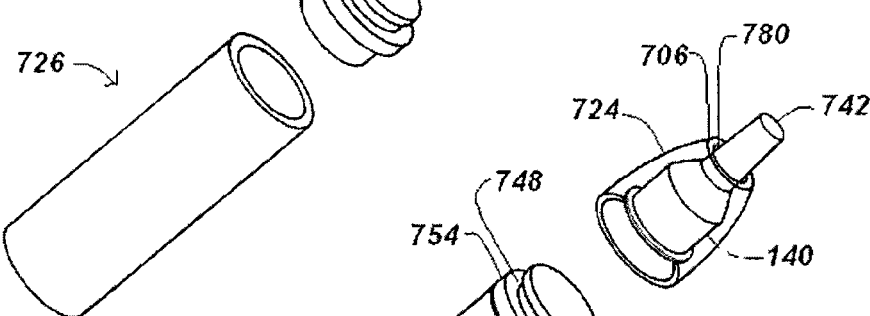
FIG. 8B is a partially exploded view of the embodiment of FIG. 8A.
Figure 8C:
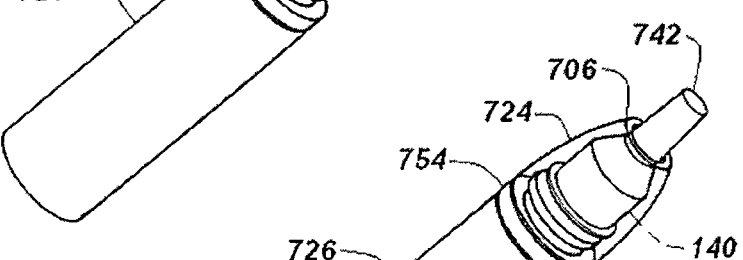
FIG. 8C is a perspective view of the embodiment of FIG. 8A.

FIGS. 8A to 8D show a storage system 700 in which cap 724 has an opening 780 through its upper end 706 through which the tip 742 of needle assembly 140 protrudes, so that it may be easily ejected from the cap. The dust sleeve may be constructed as in the previous embodiments or may be constructed as shown in FIG. 8A, in which separate plug 754 is provided to fit into upper end 750 of sleeve 726 to close off the sleeve and prevent attachment of the sleeve to the syringe unless the needle has been removed. Plug 754 includes peripheral groove 748 to receive the detents (not shown) of cap 724.

Figure 8D:
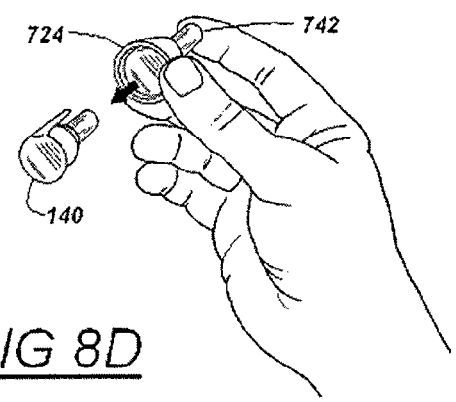
FIG. 8D is an illustration showing the ejection of a pen needle assembly from the storage cap of embodiment of FIG. 8A.

As best seen in FIG. 8D, once cap 724 is removed, pen needle assembly 140 can be ejected by simply pushing on its tip 742.

FIGS. 9A to 9D depict a storage system which combines the ejection hole 780 of the embodiment of FIGS. 8A to 8D with the hinge 256 of FIGS. 3A to 3C.

FIGS. 10A and 10B depict a storage system 800 similar to that of FIGS. 8A to 8D but having an alternative ornamental design.

Figure 11:
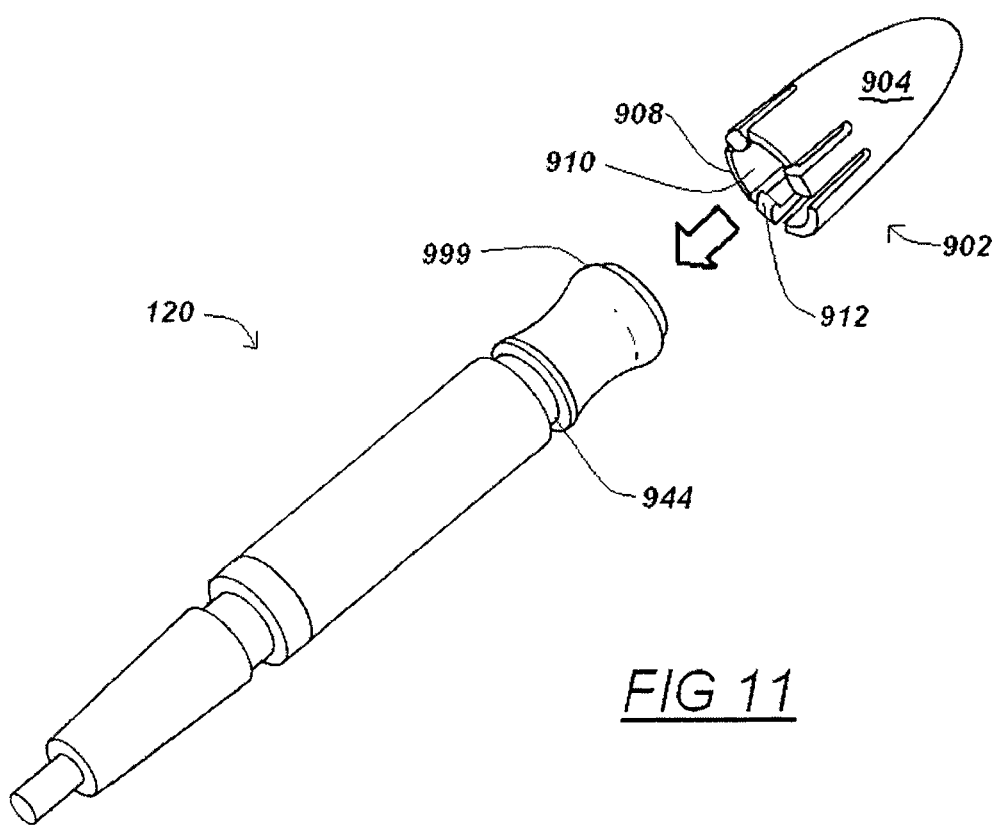
FIG. 11 is a perspective view of an empty pen needle storage cap according to an additional embodiment being temporarily affixed to the tail end of a pen delivery device syringe for keeping during use of the syringe.

FIG. 11 depicts an alternate embodiment in which cap 902 includes three integral snap detents 912 on circular end 908 of the cap's shell 904, which are adapted to flex outwardly and snap over the tail end 999 of pen delivery device syringe 120 and into peripheral groove 944, for convenient keeping while using the pen delivery device syringe. Cavity 910 receives the pen delivery device syringe's tail end 999 during this configuration, or receives the typical needle assembly during storage. As in the previous embodiments, cap 902 may be affixed to the dust sleeve (not shown) at the other end of the pen delivery device syringe, and snap detents 912 then may grasp the dust sleeve at it's peripheral groove during storage.

Other objects, features and advantages of the invention will become apparent to those skilled in the art from the above description and the accompanying drawings. It should be understood, however, that these specific examples, while teaching exemplary embodiments of the invention, are given only to illustrate and not to limit the scope of the invention. Many changes and modifications may be made while remaining within the invention's scope, which should only be limited by the appended claims.

We claim:

1. A pen needle storage system for attachment to and use with a pen delivery device syringe, said system comprising:
 a pen needle attachable to a syringe distal end;
 a tubular dust sleeve comprising a first hollow cavity for slidable placement over the syringe distal end;
 a needle assembly for enclosing the pen needle; and
 a hollow cap comprising a second hollow cavity for receiving therein the needle assembly;
 wherein said hollow cap is adapted to affix to a sleeve distal end of said tubular dust sleeve to retain the needle assembly, and said tubular dust sleeve is attachable to the pen delivery device syringe only when the pen needle is detached from the pen delivery device syringe, wherein said retention of the needle assembly and fixation of the hollow cap to the tubular dust sleeve and the tubular dust sleeve to the pen delivery device syringe defines a continuous tubular housing.

2. The system of claim 1 wherein said tubular dust sleeve is cylindrical and longitudinally aligned with said pen delivery device syringe upon receipt thereof.

3. The system of claim 2 wherein said hollow cap is tapered inwardly from said affixation to said sleeve toward a blunt terminal tip.

4. The system of claim 3 wherein said blunt terminal tip is bullet-shaped.

5. The system of claim 1 wherein said hollow cap further comprises a hinge and wherein said first and second hollow cavities are relatively rotatable about said hinge.

6. The system of claim 5 wherein said hinge is molded of a flexible polymer material.

7. The system of claim 6 wherein said tubular dust sleeve is cylindrical and longitudinally aligned with said pen delivery device syringe upon receipt thereof.

8. The system of claim 7 wherein said hollow cap is tapered inwardly from said affixation to said sleeve toward a blunt terminal tip.

9. The system of claim 8 wherein said terminal tip is bullet-shaped.

10. A method of storing a needleless pen delivery device syringe and a pen needle adapted for attachment to and use with the pen delivery device syringe, said method comprising:
 providing a tubular dust sleeve and a hollow cap, the tubular dust sleeve comprising a first hollow cavity for receiving therein a distal syringe end, the hollow cap comprising a second hollow cavity for receiving therein a needle assembly enclosing the pen needle;
 positioning said hollow cap for attachment to said tubular dust sleeve; and
 inserting the distal syringe end into the first hollow cavity to form a continuous tubular housing, wherein formation of the continuous tubular housing is prevented when the pen needle is attached to the syringe distal end.

11. A pen shaped containment system for a needleless pen delivery device syringe, comprising:
 a cap having a cap open end, a cap closed end, and a cap cavity;
 a dust sleeve having a sleeve open end, a sleeve distal end, and a sleeve cavity;
 a needle assembly enclosing a pen needle; and
 a pen delivery device syringe having a syringe distal end adapted for connection to the pen needle,
 wherein said cap open end is adapted for attachment to said sleeve distal end such that said needle assembly is retained within the cap cavity; and
 wherein said pen delivery device syringe is insertable into the sleeve open end for retention within the sleeve cavity to define a unitary tubular structure, wherein said unitary tubular structure is formable only when said pen needle is detached from said syringe distal end.

12. The pen shaped containment system of claim 11, further comprising:
 at least one accessory-storing module; and
 a second needle assembly enclosing a second pen needle,
 wherein the at least one accessory-storing module is adapted for attachment between said cap and said dust sleeve such that said second needle assembly is retained within the accessory-storing module.

13. The pen shaped containment system of claim 11, wherein the cap is attached to the dust sleeve with a living hinge proximate the cap open end and the sleeve distal end.

* * * * *